United States Patent
Hilton (10) Patent No.: US 11,532,388 B2
(45) Date of Patent: Dec. 20, 2022

(54) ANALYSIS AND DISPENSING SYSTEM

(71) Applicant: Eric Hilton, Lincoln (GB)

(72) Inventor: Eric Hilton, Lincoln (GB)

( * ) Notice: Subject to any disclaimer, the term of this patent is extended or adjusted under 35 U.S.C. 154(b) by 0 days.

(21) Appl. No.: 17/274,676

(22) PCT Filed: Sep. 10, 2019

(86) PCT No.: PCT/GB2019/052528
§ 371 (c)(1),
(2) Date: Mar. 9, 2021

(87) PCT Pub. No.: WO2020/053578
PCT Pub. Date: Mar. 19, 2020

(65) Prior Publication Data
US 2022/0051776 A1    Feb. 17, 2022

(30) Foreign Application Priority Data
Sep. 10, 2018   (GB) .................... 1814644

(51) Int. Cl.
*G16H 20/13*    (2018.01)
*A61J 1/20*    (2006.01)
(Continued)

(52) U.S. Cl.
CPC ............... *G16H 20/13* (2018.01); *A61J 1/20* (2013.01); *A61J 7/0076* (2013.01);
(Continued)

(58) Field of Classification Search
CPC .......... G16H 20/13; A61J 1/20; A61J 7/0076; G01N 33/492; G07F 13/025; G07F 17/0092
See application file for complete search history.

(56) References Cited

U.S. PATENT DOCUMENTS 8,206,340 B2    6/2012  Arefieg
2003/0174326 A1*  9/2003  Rzasa .................... G16H 40/63
                                                    356/326

(Continued)

FOREIGN PATENT DOCUMENTS

WO    2009/066288 A1    5/2009
WO    2017181287 A1    10/2017
WO    WO-2017181287 A1 *  10/2017  ............ A61J 7/0454

OTHER PUBLICATIONS

Anonymous: "Mi-nutraTM Personlised Nutrition", Nutrapharma, Feb. 14, 2016 (Feb. 14, 2016), pp. 1-5, XP055643963, Retrieved from the Internet: URL:https://nutra-pharma.co.uk/donation/mi-nutratm-personlised-nutriti on/ [retrieved on Nov. 19, 2019].

(Continued)

*Primary Examiner* — Michael Collins
(74) *Attorney, Agent, or Firm* — Young Basile Hanlon & MacFarlane, P.C.

(57) ABSTRACT

A device for dispensing a medicament and/or dietary supplement to a user comprises a housing; a sample inlet unit; a sample analysis unit; a data processing unit; and a dispensing assembly including a cartridge holder and a dispensing mechanism comprising means for dispensing a metered dose of said medicament or dietary supplement. The device may be used in a method for the customised provision of medicaments and/or dietary supplements to a user.

13 Claims, 3 Drawing Sheets

(51) Int. Cl.
*A61J 7/00* (2006.01)
*G01N 33/49* (2006.01)
*G07F 13/02* (2006.01)
*G07F 17/00* (2006.01)

(52) U.S. Cl.
CPC ......... *G01N 33/492* (2013.01); *G07F 13/025* (2013.01); *G07F 17/0092* (2013.01)

(56) References Cited

U.S. PATENT DOCUMENTS

| | | | |
|---|---|---|---|
| 2005/0043674 A1 | 2/2005 | Blair et al. | |
| 2006/0067911 A1* | 3/2006 | Nilsson | A61M 15/0045 514/14.1 |
| 2007/0255450 A1* | 11/2007 | Mazur | G07F 11/44 222/129 |
| 2012/0265591 A1* | 10/2012 | Hwang | G06Q 30/00 705/14.1 |
| 2013/0142709 A1* | 6/2013 | Lin | G01N 27/4163 422/537 |
| 2013/0149377 A1* | 6/2013 | Alfano | B65B 1/34 264/109 |
| 2013/0274576 A1 | 10/2013 | Amirouche et al. | |
| 2014/0243635 A1 | 8/2014 | Arefieg | |
| 2015/0291411 A1* | 10/2015 | Ittstein | A61J 3/002 222/1 |
| 2017/0156386 A1 | 6/2017 | Baetge et al. | |
| 2020/0375850 A1* | 12/2020 | Merril | G16H 40/20 |

OTHER PUBLICATIONS

Anonymous: "Personalised Nutrition with Nutra-Pharma", Nov. 30, 2017 (Nov. 30, 2017), page I, XP055645600, Retrieved from the Internet: URL:http://www.theworldofwork.co.uk/News/View/id/D50FOOAD-EOE7-4B90-AF56-BA3FAF6C6145 [retrieved on Nov. 22, 2019].

* cited by examiner

ANALYSIS AND DISPENSING SYSTEM

CROSS-REFERENCE TO RELATED APPLICATION(S)

This application claims priority to GB Application Patent Ser. No. 1814644.9, filed Sep. 10, 2018, the entire disclosure of which is hereby incorporated by reference.

TECHNICAL FIELD

The present invention relates to an analysis and dispensing system for the provision of medicaments and dietary supplements to a user.

BACKGROUND

The global market for dietary supplements amounted to approximately USD 132.8 billion in 2012 and is set to continue to grow. It is estimated that by 2022, the global market in this area will be worth around USD 220 billion.

Dietary supplements include vitamins, minerals, herbal products, amino acids and various other products. People take dietary supplements for a number of reasons. While some may be aware that they are deficient in one or more nutrients, many use supplements to support their general health and well-being. With a vast array of supplements available, some will select particular products to use (Vitamin C is the most popular single vitamin supplement), and others will opt for a range of supplements, for example as available in a 'multivitamin' product. However, many individuals who regularly take dietary supplements are not aware of their personal needs. They may have adequate levels of certain nutrients but have undesirably high or low levels in others. Over-the-counter supplements may therefore include various elements of which a particular individual has no need, or they may not contain enough of something in which the individual is deficient.

Precision medicine is an emerging approach for disease treatment and prevention that takes into account an individual's genetic profile, environment, and lifestyle. Through precision medicine, treatments may be tailored to an individual on the basis of diagnostic tests based on the presence, or absence, of biomarkers. Such an approach promises better clinical outcomes, safer medicines and less wastage, compared with the traditional "one-size-fits-all" approach in the medical field.

Biomarkers are used to indicate particular biological states or conditions. In the context of the present invention, quantifiable biomarkers are employed to indicate, for example, vitamin and mineral levels, protein detection, or levels of hormones, antigens and other substances which can be indicative of particular diseases.

In the nutrient field, recommended daily intake levels for number of vitamins and other nutrients, for example those considered essential for human beings are widely publicised. Determination of specific biomarkers in the blood indicates the concentration of such nutrients in the body, and a comparison with generally accepted healthy levels can indicate, for example, if a particular individual is deficient in, or has an insufficient intake of, a particular vitamin or other nutrient.

The following is a non-exhaustive list of nutrient-related biomarkers that can be quantified through analysis of a sample of blood:

Water Soluble Vitamins:
Vitamin C: ascorbic acid
Vitamin B12: VitB12, homocysteine, methylmalonic acid (MMA), transcobalamin (holoTC)
Folate: Folate (serum or RBC), homocysteine, folic acid
Vitamin B1 (thiamine)
Vitamin B3 (niacin)
Vitamin B2 (riboflavin)
Vitamin B6 (pyridoxine)
Fat Soluble Vitamins:
Vitamin A: Retinol, retinol binding protein.
Vitamin A (beta carotene)
Vitamin D: 1, 25 Hydroxycholecalciferol
Vitamin E (alpha-tocopherol)
Vitamin K1 (phytonadione)
Other Minerals:
Magnesium
Iron: Ferritin, transferrin receptor, iron, hepcidin, zinc protoporphyrin/heme ratio, haemoglobin/haematocrit.
Zinc: zinc
Iodine: Iodine, thyroglobulin, TSH, T3/T4

The analysis of blood for determining vitamin and mineral levels (through direct measurements or functional tests) is well established and there are generally accepted healthy value ranges, some examples of which are listed below.

For Vitamin D, levels of from 20 nanogram/millilitre to 50 ng/mL are generally considered as healthy; a level of less than 12 ng/mL indicates deficiency For Vitamin C (ascorbate), levels less than 0.3 mg/dL indicate significant deficiency, while levels that exceed 0.6 mg/dL indicate sufficient intake.

For Vitamin B12 (cobalamin), levels of between 200 and 900 picograms per millilitre (pg/mL) are generally considered as healthy.

For Vitamin B6 (using the reference for pyridoxal phosphate (PLP), the biological active form of vitamin B6): 5-50 micrograms/L are generally considered as healthy.

For Vitamin B1 (thiamine), using thiamine pyrophosphate (TPP): levels 2.5-7.5 micrograms/dL or 74-222 mol/L are generally considered as healthy.

For Vitamin B3 (niacin), using nicotinamide adenine dinucleotide (NAD) & nicotinamide adenine dinucleotide phosphate (NADP), a value of below 130 for the ratio of NAD/[NAD+NADP]×100 suggests deficiency.

For Vitamin A (retinol), measuring retinol, ranges of from 15 to 60 micrograms/L are generally considered as healthy, with values less than 15 mcg indicating deficiency.

For Vitamin B2 (riboflavin), using flavinadeninedinulceotide (FAD) (90% of total riboflavin in blood), 137-370 micrograms/L are generally considered as healthy, with levels less than 137 mcg/L indicating deficiency.

For Vitamin B5 (pantothenic acid), pa range from 1.6 to 2.7 mcmol/L is generally considered as healthyl, with levels less than 1.6 mcmol/L indicating deficiency.

For Vitamin E (tocopherol), using alpha-topherol levels in blood, anything less than 5 mcg/mL indicates deficiency.

For Vitamin B9, Folic acid (folate), using folate levels: 2-20 ng/mL generally considered as healthy, with levels less than 2 ng/mL indicating deficiency.

For Omega 3: measuring EPA and DHA, 8% total erythrocytes fatty acids is the target level in blood analysis.

For Omega 6, the target ratio with Omega 3 is 2:1 (in most western diets the ratio is 10:1).

For Iron the serum ferritin levels measured should not be below 20 ng/mL

In the medical field, biomarkers for a number of diseases are known, with the list below representing only a few of such.

Medicinal Markers:
Cardiac Disease/Injury: Troponin I
Renal (acute problems): Serum IL-6 and IL-8
Prostate (cancer): Prostate-specific antigen (PSA)
Ovaries (cancer): cancer antigen 125 (CA125)
Medullary Thyroid cancer: calcitonin
Liver cancer: alpha-fetoprotein (AFP)
Testicular cancer: human chorionic gonadotropin (HCG)

Blood testing in order to determine biomarkers in a person's blood generally involves the taking of a sample of blood by a trained clinician, with the sample then being transferred to a specialist laboratory for analysis. The process is time-consuming and labour-intensive.

Kits for blood sampling by an individual have become available, including kits intended for use by the individual at home. Generally, the individual will collect a blood sample from a finger or thumb, using a simple finger prick test kit, and will then send the sample to a specialist laboratory for assessment. Such kits are generally used to determine food intolerances and nutritional deficiencies, etc.

In the field of diabetes care, US 2014243635 discloses a device for enabling patient self-testing and treatment self-administration including a sampling mechanism for taking from a patient a sample that can be tested for a property indicative of a medical condition of the patient; circuitry such as a microprocessor for determining a treatment for the condition based on a test of the sample; and an administration mechanism for administering the treatment. This disclosure relates specifically to an integrated blood glucose monitor and insulin pen unit for collecting a blood sample from a patient, analysing the glucose level in the sample, calculating an insulin dosage based on the based on the insulin level, if appropriate, and administering the calculated dosage. Stored protocols and criteria may be employed to determine whether treatment is required. Numerous variations of the unit are mentioned, including multi-medicament possibilities, for example vitamin assortments for wellness programs, which vitamin assortments may be administered orally or by injection.

Also in the field of diabetes care, U.S. Pat. No. 8,206,340 relates to a portable insulin injection pen and blood glucose monitoring device integrated into a single unit for testing and treating diabetes symptoms. A blood glucose monitoring system for receiving a sample of the user's blood and detecting its glucose level, an insulin injection mechanism for administering an insulin injection, and a microprocessor that calculates an insulin dosage appropriate to the detected blood glucose level and sets the insulin injection mechanism to administer the calculated insulin dosage, are included in the device; the microprocessor calculates treatment regimens specific to a particular user based on the detected blood glucose level and displays the treatment regimens on an LCD display.

US2015291411 relates to a device for dispensing, for example, a nutritional supplement or a medication, based on the specific requirements of an individual. The device may include the following: a formulation and/or dose generating unit, a supplies unit, a mixing unit, an input unit, an evaluation unit, a sensor unit, a communication unit; an environment parameter capturing unit; a formulation output unit, a packaging generating unit and an injection unit.

SUMMARY

The present invention relates to a device for use in a home or clinical environment, which device is adapted to analyse a blood sample for specific biomarkers, to determine an individual's need for a dietary supplement or medicament, and to dispense a dietary supplement or medicament to a user.

Thus, in a first aspect, the present invention provides a device for dispensing a medicament or dietary supplement to a user, said device comprising:
a housing;
a sample inlet unit;
a sample analysis unit;
a data processing unit; and
a dispensing assembly including a cartridge holder and a dispensing mechanism comprising means for dispensing a metered dose of said medicament or dietary supplement.

The sample analysis unit may be selected from, for example, a miniature mass spectrometer, a miniature optical spectrometer, a miniature NMR spectrometer and a photonic lab-on-a-chip optical sensor.

In a second aspect, the present invention provides a method for providing to a user customised dietary supplements or medicaments, said method comprising:
providing a device in accordance with the first aspect of the present invention;
loading said device with a cartridge containing individual packages of medicaments or dietary supplements;
introducing into said device a sample of the user's blood for biomarker analysis; and
enabling said device to dispense a dietary supplement or medicament.

In a third aspect, the present invention provides a kit for the provision of dietary supplements or medicaments, comprising:
a device in accordance with the first aspect of the present invention; and
a cartridge for holding dietary supplements and/or medicaments; and
packages of dietary supplements or medicaments for use with said device.

BRIEF DESCRIPTION OF THE DRAWINGS

The device of the present invention is further described with reference to the accompanying Figures, which are provided purely for the purposes of illustration.

Figure 1:
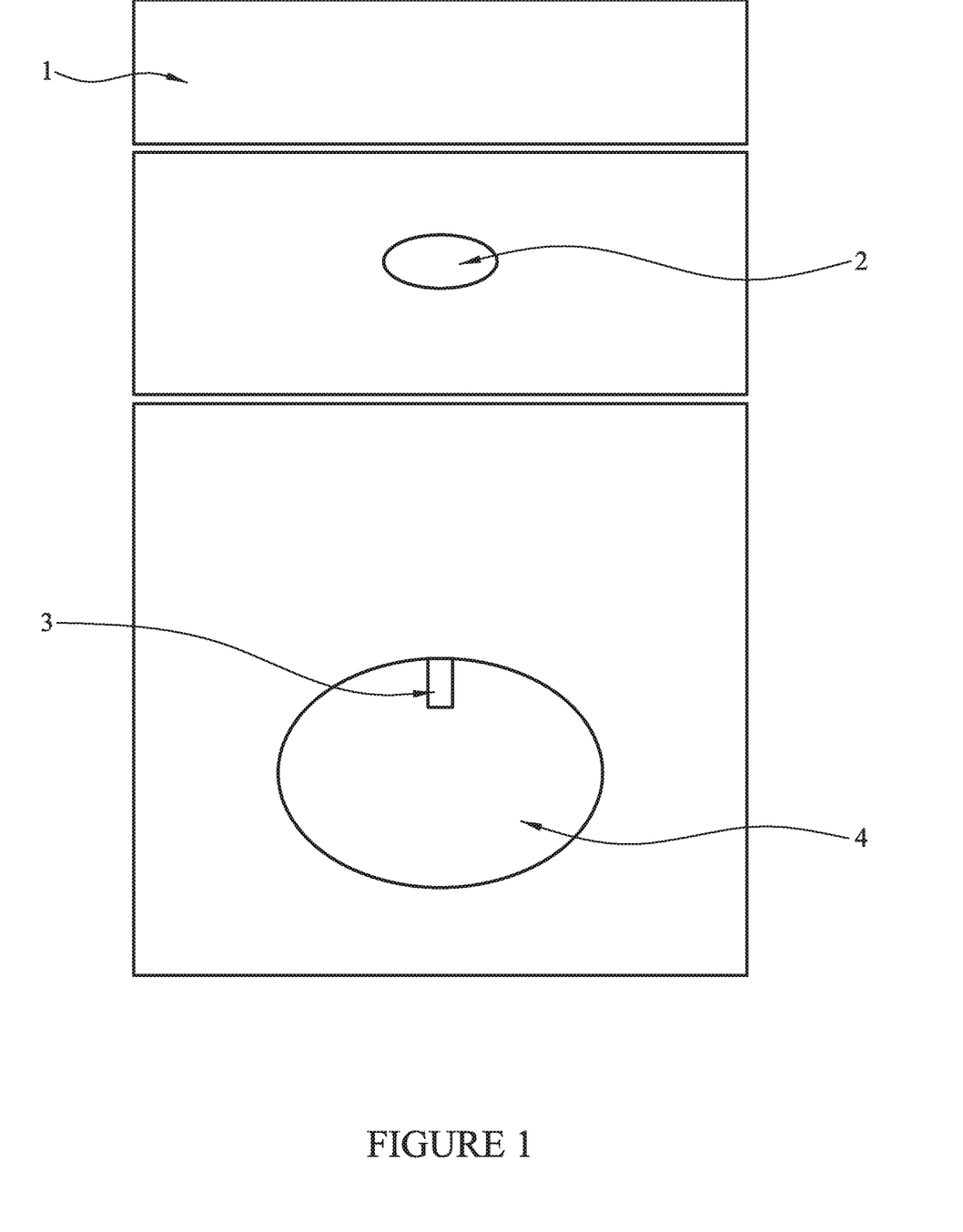
FIG. 1 is an illustration of an example of a housing in accordance with the device of the present invention.

With reference to FIG. 1, the housing of the device of the present invention is, in this example, cylindrical. A lid (1), which may be hinged, provides on removal or opening, an entry point for receipt of medicaments and/or dietary supplements. An inlet port (2) is provide for receiving a sample for analysis, and a recess (4) allows for provision of a receptacle into which medicaments and/or dietary supplements are dispensed through an outlet (3).

Figure 2:
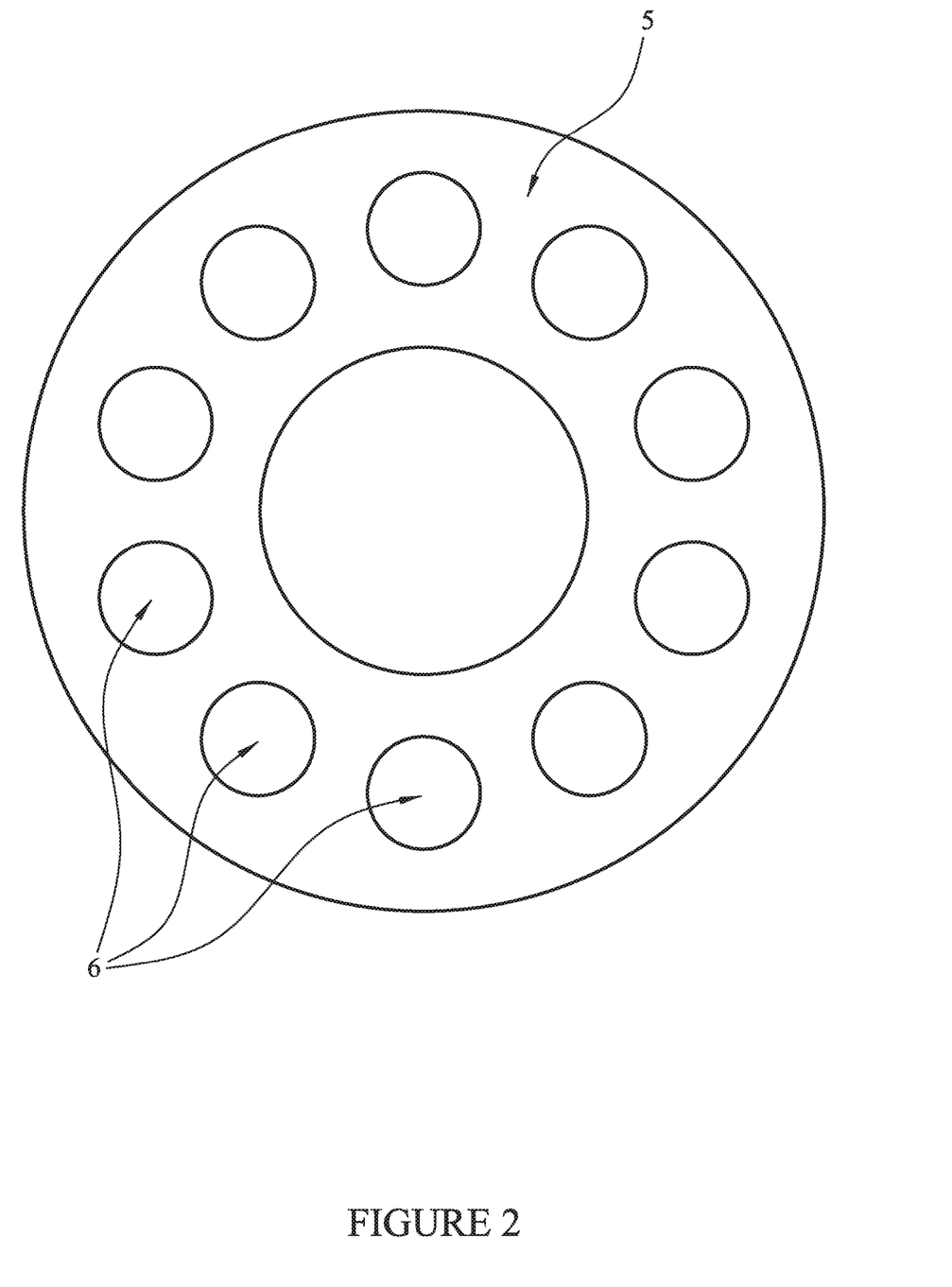
FIG. 2 is a plan view of an example of a cartridge for use with the device of the present invention.

In the example of FIG. 2, a cartridge (5) is cylindrical and is provided with multiple cylindrical chambers (6), into which medicament and/or dietary supplement packages are placed.

Figure 3:
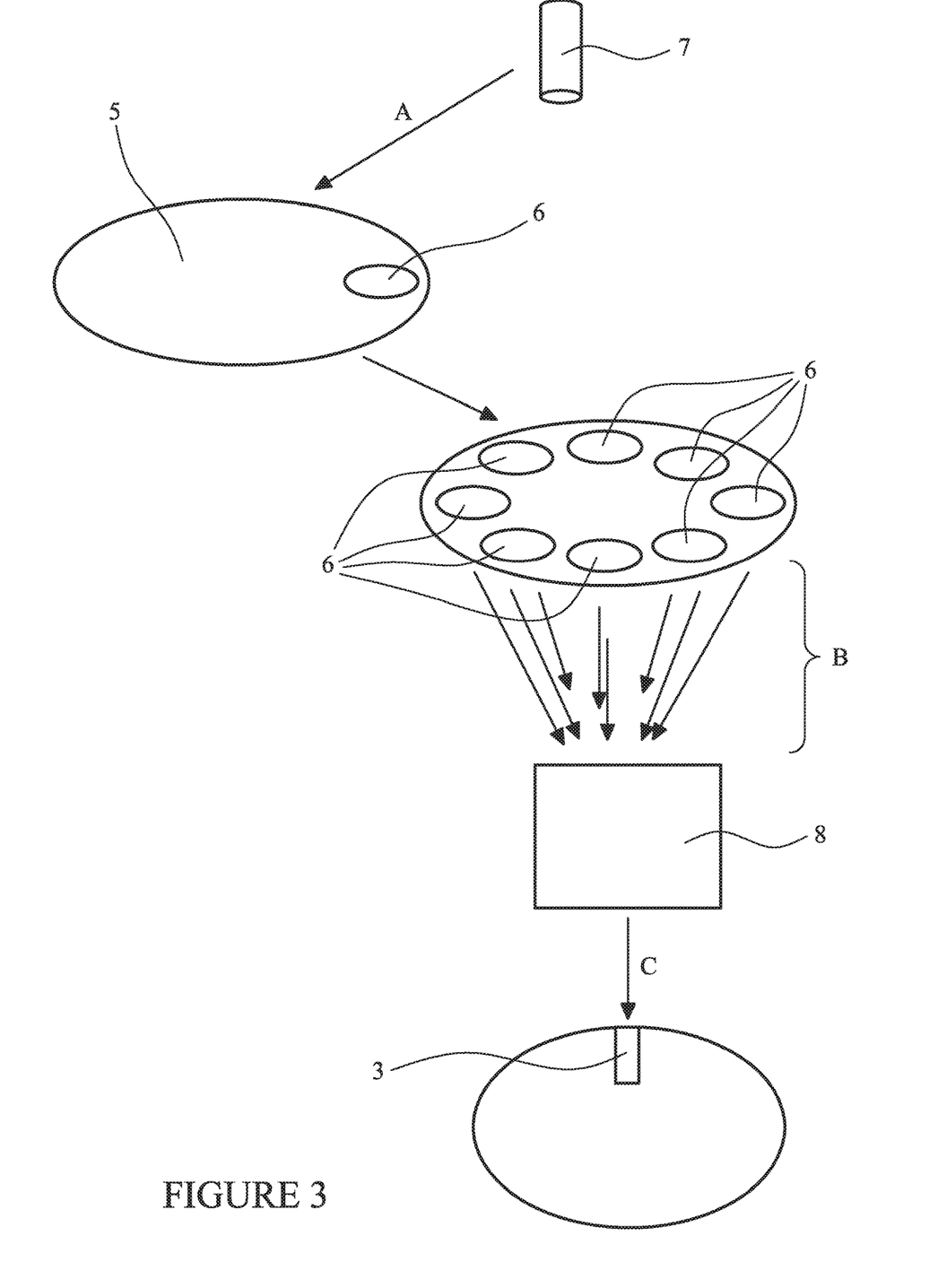
FIG. 3 is an illustration of an example of a dispensing pathway within the device of the present invention.

With reference to FIG. 3, in use of the device of the present invention cartridges (7) are placed into the chambers (6) of the cartridge (5) (Step A). Metered doses of medicaments and/or dietary supplements drawn out from the chambers (for example through pipes or tubes (not shown), with the assistance of vacuum pump (not shown)) are delivered to a micronising chamber (8) (Step B). The combined medicaments and/or dietary supplements are then dispensed through the outlet (3) (Step C).

DETAILED DESCRIPTION

Device

The device of the present invention is a Precision Nutrition device, providing nutrition for the right person at the right time with the right nutrients and/or therapy. It provides tailored treatment via diagnostic tests based on the presence (or absence) of biomarkers and does so by analysing a blood droplet, the results from which produce a metered dose of the medicaments and/or dietary supplements required by the individual user. Medicaments and/or dietary supplements are provided in cartridge form for dispensing from the device, as described further below.

In an embodiment, the device of the present invention is intended to be suitable for personal use, for example in the home of a user. It will therefore have an aesthetically pleasing appearance, for display for example alongside other small home appliances. In other embodiments, the device of the present invention is adapted for use in a clinical or commercial (e.g., workplace or health club) environment, with multiple users.

The device comprises:
a housing;
a sample inlet unit;
a sample analysis unit selected from, for example, a miniature mass spectrometer, a miniature spectrophotometer, a miniature RAMAN spectrometer, a miniature NMR spectrometer, and a photonic lab-on-a-chip optical sensor;
a data processing unit; and
a dispensing assembly including a cartridge holder and a dispensing mechanism comprising means for dispensing a metered dose of said medicament or dietary supplement.

Other types of miniature optical spectrometer may be suitable for inclusion in the device of the present invention.

In some embodiments, the device of the present invention further comprises an interactive screen for the input and display of information. In other embodiments, the input and display of information may be facilitated by an external electronic device such as a personal computer or hand-held device. In the latter case, the device of the present invention may not include an interactive screen.

Communication within the device and between the device and any external electronic device may be by any known means, including via cable media or wireless media.

In some embodiments, data generated in the device of the present invention is stored in an external data storage facility, such as a cloud storage facility. Cloud services are widely available, form a range of providers. One provider is PeaSoup, Weybridge, Surrey, a cloud specialist company providing a completely secure cloud with end-to-end encryption.

In some embodiments, data generated in the device of the present invention is stored internally within the device, in the data processing unit.

In some embodiments, the data store comprises a database of a user's records, for example comprising information from an initial blood screen of a user and/or information from a personal profile of the user.

The data store will generally comprise blood analysis data threshold values for indicating, for example, where nutrient deficiencies exist.

In some embodiments, the data store may log blood analysis data over time to indicate a user's progress and predict ongoing dietary supplement or medication needs.

In some embodiments, the present device may be provided with a unique identifier such as a unique identification code.

In some embodiments, the device of the present invention is used in combination with a mobile app. By 'app' is meant a software application. Thus, the mobile app is an application associated with the device of the present invention, and comprises software designed to run on a smartphone or another mobile device such as a tablet or watch.

Sample Analysis Unit

A key feature of the device of the present invention is sample analysis unit, within which biomarkers in a provided sample are quantified.

In preferred embodiments, the sample analysis unit is selected from:
a miniature mass spectrometer;
a miniature spectrophotometer;
a miniature RAMAN spectrometer;
a miniature NMR spectrometer; and
a photonic lab-on-a-chip optical sensor.

Mass spectrometry (MS) is a powerful technique for chemical and biological analysis. By measuring the mass and charge of ions, MS quantifies the relative abundance of ions in an analysed sample. Traditionally, MS has been performed in analytical laboratories by large-scale mass spectrometers; however, the increasing demands of in situ analysis in various fields has led to the development of miniature mass spectrometers. Commercially available miniature mass spectrometers are suitable for inclusion in the device of the present invention. Such miniature mass spectrometers are available for example from BaySpec, Inc, San Jose, Calif. (e.g., 'Portability'™ mass spectrometers) and from SCIEX UK Ltd., Warrington, Cheshire (e.g., 'Topaz'™ mass spectrometers).

Spectrophotometers (also known as UV-Vis spectrometers) and RAMAN spectrometers are examples of optical spectrometers.

The principles of UV-Vis spectrometry are well known. The technique relies on the measurement of the attenuation of a beam of light after it passes through a sample or after reflection from a sample surface. A given biomarker in the provided sample will give a characteristic spectrum and comparison with a reference spectrum of said biomarker.

RAMAN spectroscopy is based on the interaction of light with the chemical bonds in a substance. In this technique, a high intensity laser light source is applied to the provided sample and a RAMAN spectrum of scattered light (at different wavelengths to the laser source) is produced. The RAMAN spectrum represents a distinct chemical footprint for a particular substance, and quantitative analysis is possible by comparing peak intensities with reference spectra.

Commercially available optical spectrometers are suitable for inclusion in the device of the present invention. Such optical spectrometers are available for example from IS- Instruments Limited, Tonbridge, Kent (e.g., the 'MSP1000' miniature spectrometer (minispec)), and from Knight Optical (UK) Ltd., Harrietsham, Kent (e.g., the 'Blueshift', 'Shooting star', 'Supernova', Redshift, 'Nebula', 'Raman galaxy' and 'Knight' mini spectrometers).

NMR spectroscopy relies on the spin properties of nuclei. Resonance occurs when nuclei possessing spin are subject to a static magnetic field and then exposed to radio waves that flip the direction of spin of the nuclei. The energy required to change the alignment may be compared to a standard and used to produce a characteristic NMR spectrum. Commercially available NMR spectrometers are suitable for inclusion in the device of the present invention. One such NMR spectrometer is the 80 MHz 'Spinsolve 80' NMR spectrometer, available from Magritek GmbH, Aachen, Germany.

Photonic 'lab-on-a-chip' (PhLoC) optical sensors combine photonic integrated circuits with lab-on-a-chip technology and comprise a miniaturised biosensor based on a photonic integrated circuit with biochemical sensors. Commercially available PhLoC optical sensors are suitable for inclusion in the device of the present invention, such as are available for example from ITL Limited, Ashford, Kent.

Any of the above analysers may be incorporated into the device of the present invention.

Dispensing Assembly

The device of the present invention includes a dispensing assembly including a cartridge holder and a dispensing mechanism comprising means for dispensing a metered dose of said medicament or dietary supplement.

The cartridge holder is adapted to contain removable cartridges containing medicaments and/or dietary supplements.

A removable cartridge may for example comprise a multi-chambered cylinder. The cartridge holder may comprise, for example, from 6 to 20 chambers. Each chamber of the cartridge is adapted to hold powdered or liquid medicament or dietary supplement, which may be contained, for example, in a package previously sealed by means of a foil or other seal, said seal being removed when the package is placed into the removable cartridge (for example before insertion of the removable cartridge into the device of the present invention). Medicament packages may be identified using an anti-counterfeit technology, for example with anti-counterfeit marking on the package and a reader built in to the device of the present invention. Such anti-counterfeit technology is available for example from SofMat Ltd, Brigg, UK.

The dispensing assembly is adapted to dispense metered doses of medicaments and/or dietary supplements. This can be achieved in a number of ways and will generally involve releasing medicaments and/or dietary supplements from a cartridge within the cartridge holder, through a metered dose aperture, for example in the base of the cartridge holder, or in the cartridge itself.

In one embodiment, the base of the cartridge holder may be rotatable and include a metered dose aperture. In such case, the cartridge may be held in the cartridge holder in a fixed position, the base of the cartridge holder being rotatable in order to align a chamber with the metered dose aperture, facilitating release of a medicament or dietary supplement. In another embodiment, the cartridge itself may comprise a metered dose aperture. In such case, a part of the cartridge housing the chambers may be rotatable for alignment of a chamber with the metered dose aperture, or a part of the cartridge including the metered dose aperture may be rotatable for alignment of the metered dose aperture with a chamber.

The dispensing mechanism comprises means for drawing out a metered dose of medicament or dietary supplement from its chamber, when aligned with the metered dose aperture. Such means may comprise, for example, a vacuum pump or a fan. The dispensing mechanism may further comprise means for mixing and/or further processing medicaments and dietary supplements. For example, the dispensing mechanism may further comprise a microniser unit for micronising and mixing together the metered doses of medicaments and/or dietary supplements before delivery through an aperture in the dispensing mechanism, for example into a vessel placed in the recess of the housing. Thus, a personalised mix of medicaments and/or dietary supplements is dispensed.

Housing

The device of the present invention includes at least the sample analysis unit, data processor and dispensing assembly within a housing. Preferred features of the housing are recited below, but the housing may be of any material, size and shape capable of housing the other components of the device.

The housing may be for example a plastic, carbon fibre or metal casing within which other components of the device are housed. The housing may be generally cylindrical in shape, with a bottom end, a curved side, and a top end, the bottom and top ends being generally circular or elliptical, but it may of course take various forms and shapes including cube, cuboid, cone, pyramid, etc., generally with a flat bottom end (base). Any reference herein to a cylinder is not intended to impart any limitation on the shape of the housing.

The housing may be provided with a lid, for example, a hinged lid. The cartridge holder may be disposed for example immediately beneath the lid such that said cartridge holder is accessed by removing or opening the lid.

The housing will generally include an inlet port for receiving a sample for analysis, an entry point for receipt of a cartridge containing one or more medicaments and/or dietary supplements, and a recess for holding a receptacle into which medicaments and dietary supplements may be dispensed. It may also include any or all of an interactive touch screen; an information display panel; one or more control buttons such as a power button, a wifi switch, and process instruction buttons (to instruct the device to follow a particular programme, for example); an electrical socket; and a USB port. In one embodiment, the touch screen comprises and on/off pad and a display panel for presenting information to the user (for example, to tell the user that blood is being analysed).

Sample Inlet Unit

The device of the present invention includes a sample inlet unit.

The sample inlet unit may comprise an accessible chamber, accessed through the inlet port in the housing. The inlet port may comprise a slot, but can be in any form, size, or shape that will allow insertion of the sample for analysis. The sample inlet unit may comprise means for drawing the sample for analysis into the device; for example, it may comprise a vacuum source.

Suitably, the vacuum inlet comprises a vacuum turbo pump, one example of which is the HiPace®80 turbopump as manufactured by Pfeiffer Vacuum GmbH.

The sample for analysis by the device of the present invention is typically a blood sample obtained from the user through skin puncture and loaded on, for example, solvent-charged filter paper.

Suitable filter papers for dry blood sampling are commercially available, or they may be custom-made.

Alternatively, the sample for analysis comprises a blood separation membrane carrying the blood sample. Suitable blood separation membranes may comprise, for example, silicon or porous Teflon/PTFE (polytetrafluoroethylene)/PDMS (polydimethylsiloxane) membranes, examples of which are commercially available, or they may be custom-made.

Suitable filter papers and membranes will generally be in flat card form and may be of any shape. They may comprise a clip or similar component for ease of handling.

In another embodiment, the sample for analysis may be a simple blood drop, contained in a suitable receptacle such as a capillary tube.

Skin puncture may be achieved by any suitable means, such as for example through the use of a lancet device for drawing capillary blood. Generally, the sample will come from a finger of a user but other common sites for lancing include the palm of a user's hand or the user's forearm or thigh.

Lancets of the type widely used by diabetic patients are suitable for use with the device of the present invention. One example of a suitable lancet is the 'tinyBoy' lancet, by Health Innovation Ideas, California.

Data Processing Unit

The data processing unit comprises software which compares data obtained from the sample analysis unit with stored reference data and identifies, for example, peaks and troughs in the biomarker spectra. This results in a binary reading which instructs the dispensing system in the release of metered doses of medicaments and/or dietary supplements.

For example, in one embodiment, the software may direct an electronic output to a switch enabling the medicament or dietary supplement to be dispensed.

In other embodiments, the dispensing system is user-initiated, i.e., information obtained from sample analysis may be conveyed to the user, for example via a display panel or interactive screen on the device or via an external device as referred to above. In the latter cases, user confirmation enables a medicament or dietary supplement to be dispensed.

The data processing unit may comprise more than one cooperating data processor.

The device of the present invention may be programmed by an external unit, for example by a personal computer or by a suitable mobile device, for example before first use.

Advantageously, a user will generate a personal profile by completing a detailed health and lifestyle questionnaire via the external unit. Analysis of the completed questionnaire will dictate the medicaments and/or dietary supplements likely to be required or desired by the user, and therefore the nature of the cartridges required. The data processing unit within the device may then be programmed in respect of the biomarkers appropriate for the user.

It may be desirable for the user to first have a full blood screen carried out, in order to identify any areas of need of which the user is unaware.

Method

In a second aspect, the present invention provides a method for providing to a user a dietary supplement or medicament, said method comprising:

providing a device in accordance with the first aspect of the present invention;

loading said device with a cartridge containing individual packages of medicaments or dietary supplements;

introducing into said device a sample of the user's blood for biomarker analysis; and enabling said device to dispense a dietary supplement or medicament.

As described above, the device of the present invention comprises a cartridge holder adapted to contain removable cartridges containing medicaments and/or dietary supplements, a removable cartridge for example comprising a multi-chambered cylinder, each chamber of which is adapted to hold a package of powdered or liquid medicament or dietary supplement.

Thus, in accordance with the present method, a user loads a filled cartridge into the cartridge holder of the device and introduces a blood sample into the device through the inlet. As detailed above, the blood sample may be obtained for example through skin puncture and loaded on, for example, solvent-charged filter paper.

Analysis of the blood sample within the device will identify the user's needs for particular dietary supplements and/or medicaments. While these may be automatically delivered by the device, in some embodiments the dispensing of dietary supplements and/or medicaments is user-enabled, for example, by a positive answer to a question posed to the user through a touch panel on the device or via an external electronic device.

Kit

In a third aspect, the present invention provides a kit for the provision of dietary supplements and/or medicaments, comprising:

a device in accordance with the first aspect of the present invention;

a cartridge for holding dietary supplements and/or medicaments; and packages of dietary supplements and/or medicaments for use with said device.

The kit may further comprise one or more of a lancet; solvent-charged filter paper; a blood separation membrane, and a receptacle such a capillary tube, adapted to receive a blood sample.

Embodiments of the present invention are described in the following clauses:

A device for dispensing a medicament or dietary supplement to a user, said device comprising:

a housing;

a sample inlet unit;

a sample analysis unit;

a data processing unit; and a dispensing assembly including a cartridge holder and a dispensing mechanism comprising means for dispensing a metered dose of said medicament or dietary supplement.

2. A device as disclosed in clause 1, wherein the housing is generally cylindrical in shape and has an inlet port for receiving a sample for analysis, an entry point for receipt of medicaments and/or dietary supplements, and a recess for holding a receptacle into which medicaments and dietary supplements are dispensed.

3. A device as disclosed in clause 1 or clause 2, wherein the sample inlet unit comprises a chamber accessible through an inlet port in the housing, and a vacuum source.

4. A device as disclosed in any one of clauses 1-3, wherein the sample analysis unit comprises a residual gas analyser comprising a probe including an ionisation chamber, a mass analyser, and a detector unit; and an electronics control unit.

5. A device as disclosed in any one of clauses 1-4, wherein the data processing unit comprises software adapted to compare mass spectra generated by the sample analysis unit with stored mass spectra of specified biomarkers and instruct the dispensing assembly in the release of one or more medicaments and/or dietary supplements.

6. A device as disclosed in any one of clauses 1-5, wherein the dispensing assembly comprises a cartridge holder and a dispensing mechanism.

7. A device as disclosed in clause 6, wherein the cartridge holder comprises a rotatable base and a metered dose aperture.

8. A device as disclosed in clause 7, wherein the dispensing mechanism comprises means for drawing out a metered dose of medicament or dietary supplement from a chamber of a multi-chambered cartridge contained in the cartridge holder.

9. A device as disclosed in clause 8, wherein the means for drawing out a metered dose of medicament or dietary supplement from a chamber of a multi-chambered cartridge contained in the cartridge holder comprises a vacuum pump or a fan.

10. A device as disclosed in any one of clauses 6-9, wherein the dispensing mechanism comprises a microniser unit for micronising and mixing together the metered doses of medicaments and/or dietary supplements before delivery through the metered dose aperture.

The invention claimed is:

1. A device for dispensing a medicament or a dietary supplement to a user, the device comprising:
    a housing;
    a sample inlet unit;
    a sample analysis unit selected from a miniature mass spectrometer, a miniature spectrophotometer; a miniature RAMAN spectrometer; a miniature NMR spectrometer; and a photonic lab-on-a-chip optical sensor;
    a data processing unit; and
    a dispensing assembly including a cartridge holder and a dispensing mechanism comprising means for dispensing a metered dose of the medicament or the dietary supplement, wherein the cartridge holder comprises a rotatable base and a metered dose aperture and the dispensing mechanism comprises a micronizer unit for micronizing and mixing together metered doses of the medicament or the dietary supplement before delivery through the metered dose aperture.

2. The device as claimed in claim 1, further comprising an interactive screen for input and display of information.

3. The device as claimed in claim 1, wherein the housing is generally cylindrical in shape and has an inlet port for receiving a sample for analysis, an entry point for receipt of the medicament or the dietary supplement, and a recess for holding a receptacle into which the medicament and the dietary supplement are dispensed.

4. The device as claimed in claim 1, wherein the sample inlet unit comprises a chamber accessible through an inlet port in the housing.

5. The device as claimed in claim 4 wherein the sample inlet unit further comprises a vacuum source.

6. The device as claimed in claim 1, wherein the data processing unit comprises software adapted to compare spectra generated by the sample analysis unit with stored spectra of specified biomarkers.

7. The device as claimed in claim 6, wherein the data processing unit is adapted to instruct the dispensing assembly to release of one or more medicaments and dietary supplements.

8. The device as claimed in claim 6, wherein the data processing unit is adapted to provide information to the user via the device or via an external device.

9. The device as claimed in claim 1, wherein the dispensing mechanism comprises means for drawing out the metered dose of the medicament or the dietary supplement from a chamber of a multi-chambered cartridge contained in the cartridge holder.

10. The device as claimed in claim 9, wherein the means for drawing out the metered dose of the medicament or the dietary supplement from the chamber of the multi-chambered cartridge contained in the cartridge holder comprises a vacuum pump or a fan.

11. A method for providing to a user one or more dietary supplements and medicaments, said method comprising:
    providing a device in accordance with claim 1;
    loading the device with a cartridge containing individual packages of medicaments or dietary supplements;
    introducing into the device a sample of blood of the user for biomarker analysis; and
    enabling the device to dispense a dietary supplement or medicament.

12. A kit for the provision of one or more dietary supplements and medicaments, comprising:
    a device in accordance with claim 1;
    a cartridge for holding the one or more dietary supplements and medicaments; and
    packages of dietary supplements or medicaments for use with said device.

13. The kit as claimed in claim 12, further comprising one or more of a lancet; solvent-charged filter paper; a blood separation membrane, and a receptacle adapted to receive a blood sample.

* * * * *